United States Patent
Gericke et al.

(10) Patent No.: US 6,288,104 B1
(45) Date of Patent: Sep. 11, 2001

(54) PHARMACEUTICAL COMPOSITIONS CONTAINING MESEMBRINE AND RELATED COMPOUNDS

(75) Inventors: Nigel Peter Gericke, Cape Town; Ben-Erik Van Wyk, Johannesburg, both of (ZA)

(73) Assignee: African Natural Health CC, Cape Town (ZA)

( * ) Notice: Subject to any disclaimer, the term of this patent is extended or adjusted under 35 U.S.C. 154(b) by 0 days.

(21) Appl. No.: 09/194,836

(22) PCT Filed: Jun. 3, 1997

(86) PCT No.: PCT/GB97/01493
§ 371 Date: Mar. 22, 1999
§ 102(e) Date: Mar. 22, 1999

(87) PCT Pub. No.: WO97/46234
PCT Pub. Date: Dec. 11, 1997

(30) Foreign Application Priority Data
Jun. 4, 1996 (ZA) .................................................. 06/4595

(51) Int. Cl.[7] .................................................. A61K 31/40
(52) U.S. Cl. .......................................... 514/421; 548/512
(58) Field of Search .............................. 514/421; 548/512

(56) References Cited

FOREIGN PATENT DOCUMENTS

| 3604112A1 | 8/1987 | (DE) . |
|---|---|---|
| 46-43538 | 12/1971 | (JP) . |
| 46-43539 | 12/1971 | (JP) . |

OTHER PUBLICATIONS

Taguchi et al., "Synthesis of Octahydroindole Derivatives," Tetrahedrom Letters, 55:5763–5766 (1968).

Jeffs et al., "Total Syntheses of (±)–Joubertinamine, and (±)–N–Demethylmesembrenone," J. Org. Chem. 48:3861–3863 (1983).

Capps et al., "Sceletium Alkaloids, Part 7.[1] Structure and Absolute Stereochemistry of (−)–Mesembrane and 3'-Methoxy–4'-O-methyljoubertiamine, Two Minor Bases from S. Namaquense L. Bolus: X-Ray Analysis of (−)-Mesembrane Hydrochloride Monohydrate," J. Chem. Soc. Perkins Trans. 8:1098–1104 (1977).

Langlois et al., "Recherches Dans La Serie Des Aryl–3 Pyrrolidines–II, Syntheses de Produits Apparentes a la Mesembrine et a La Crinine," Tetrahedron 27:5641–5652 (1971).

Taguchi et al., "Synthesis of Octhydroindole Derivatives," Chem. Pharm. Bull. 18:1008–1014 (1970).

Kruger et al., "Minor Alkaloids from *Sceletium Strictum* L. Bol. The Structure of N–Demethylmesembrenol and N–Demthylmesembranol," Journal of the South African Chemical Institute XXIV:235–237 (1971).

Jeffs et al., "Sceletium Alkaloids. VI. Minor Alkaloids of *S. namaquense* and *S. strictum*," J. Org. Chem. 39:2703–2710 (1974).

Pfaffli et al., "Demethylierungen am Mesembrine," Helvetica Chimica Acta 56:347–355 (1973).

Smith et al., "Psychoactive constituents of the genus Sceletium N.E.Br. and otehr Mesembryanthemaceae: a review," Journal of Ethnopharmacology 50:119–130 (1996).

Hoshino et al., "Synthesis of Sceletium and Amaryllidaceae Alkaloids, (±)–Mesembrine and (±)–Dihydromaritidine, (±)Epidihydromaritidine, (±–Elwesine, and (±)–Epielwesine[1])," Chem. Pharm. Bull. 35:2734–2743 (1987).

*Primary Examiner*—Dwayne C. Jones
*Assistant Examiner*—C. Delacroix-Muirheid
(74) *Attorney, Agent, or Firm*—Clark & Elbing LLP

(57) ABSTRACT

There is disclosed the use of mesembrine and related compounds (e.g. mesembranol, mesembranone) as scrotonin-uptake inhibitors, pharmaceutical compositions comprising such compounds or dry material or an extract of plants from the Mesembryanthemaceae family (e.g. Sceletium (Aizoaceae) tortuosum) containing a standardized content of said compounds, for use in the treatment of depressive states, psychological or psychiatric disorders with an anxiety component, alcohol and drug dependence, bulimia nervosa and obsessive-compulsive disorders. Also disclosed are new derivatives of mesembrine.

11 Claims, 4 Drawing Sheets

|  | IC50 | $K_i$ | Slope |
|---|---|---|---|
| Imipramine HCl | 2.58E-08 | 1.80F-08 | -0.94 |
| 18639 | 5.20E-03 | 3.02E-03 | -0.63 |

|  | IC50 | $K_i$ | Slope |
|---|---|---|---|
| Imipramine HCl | 2.48E-08 | 1.53E-08 | -0.91 |
| 18623 | 2.18E-02 | 1.34E-02 | -0.58 |

|  | IC50 | $K_i$ | Slope |
|---|---|---|---|
| Imipramine HCl | 2.48E-08 | 1.53E-08 | -0.91 |
| 18622 | 1.57E-02 | 9.68E-03 | -0.75 |

PHARMACEUTICAL COMPOSITIONS CONTAINING MESEMBRINE AND RELATED COMPOUNDS

BACKGROUND OF THE INVENTION

This invention relates to the use of mesembrine and related compounds as serotonin-uptake inhibitors, to pharmaceutical compositions comprising as an active ingredient dry material or an extract of a plant of the family Mesembryanthemaceae, standardised as to its active content, and to new compounds.

It is known that the naturally occurring alkaloid mesembrine is useful as a medicament having CNS-stimulating action (see JP71043539 to Tanabe Seiyaku Company Limited).

It is also known that a plant and plant products known colloquially as "kougoed", "channa" or "kanna" in the Cape of South Africa, are used traditionally by some communities as inebriants, sedatives and to elevate mood. The plants called "kougoed", "channa" or "kanna" are all members of the family Mesembryanthemaceae, and contains varying amounts of (−)-mesembrine and related alkaloids.

An article entitled Psychoactive constituents of the genus Sceletium N.E.Br. and other Mesembryanthemaceae: a review, by Smith et al, in Journal of Ethnopharmacology, 50 (1996), Pages 119 to 130, reviews the historical data recorded over 300 year period of the use of Sceletium plants in psychoactive preparations, describes techniques for the preparation and use of "kougoed" from plants of Sceletium and documents the subjective experiences of a number of contemporary users. The alkaloid distribution in Sceletium and other members of the family Mesembryanthemaceae are also considered. Chemical studies have indicated as many as nine alkaloids in Sceletium, which fall into three distinct structural categories.

SUMMARY OF THE INVENTION

According to a first aspect of the invention there is provided the use of a compound having the formula I

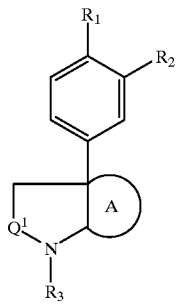

wherein the ring A is selected from the group consisting of:

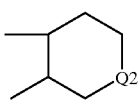 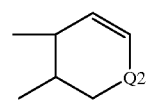 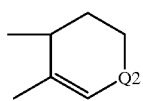

$R_1$ and $R_2$ are independently selected from H, OH, $OCH_3$ and $O(CH_2)_nCH_3$;
$R_3$ is selected from H, $CH_3$ and $(CH_2)_nCH_3$;
n is an integer from 1 to 6;
and $Q_1$ and $Q_2$ are independently selected from $CH_2$, C=O and CHOH; in the manufacture of a medicament for the treatment of diseases that respond to treatment with a serotonin-uptake inhibitor.

In their role as serotonin-uptake inhibitors, these compounds may be used in the treatment of mild to moderate depression, psychological and psychiatric disorders where anxiety is present, major depressive episodes, ie single episode and recurrent depression with associated anxiety, in alcohol and drug dependence, in the treatment of bulimia nervosa, and in the treatment of obsessive-compulsive disorders.

According to a second aspect of the invention there is provided a pharmaceutical composition in unit dosage form comprising a serotonin-uptake inhibitor having the formula I as set out above, in a dose of from 20 micrograms to 2 milligrams inclusive, preferably in a dose of from 50 micrograms to 500 micrograms inclusive, more preferably in a dose of from 100 micrograms to 300 micrograms inclusive.

According to a third aspect of the invention there is provided a method of treating diseases that respond to treatment with a serotonin-uptake inhibitor comprising administering to a patient in need thereof an effective amount of a compound having the formula I as set out above.

According to a fourth aspect of the invention there is provided a pharmaceutical composition comprising as an active ingredient plant material or an extract of a plant of family Mesembryanthemaceae, containing in each unit dose an amount of from 20 micrograms to 2 milligrams inclusive, preferably from 50 micrograms to 500 micrograms inclusive, more preferably from 100 micrograms to 300 micrograms inclusive, of a compound selected from the group consisting of mesembrine, mesembranol and mesembranone, or a mixture of two or more thereof.

The plant of the family Mesembryanthemaceae is preferably a plant of the genus Sceletium, more preferably a plant of the species Sceletium tortuosum(L.) N.E. Br.

The pharmaceutical composition of the invention is also useful in the treatment of mild to moderate depression, psychological and psychiatric disorders where anxiety is present, major depressive episodes, ie single episode and recurrent depression with associated anxiety, in alcohol and drug dependence, in the treatment of bulimia nervosa, and in the treatment of obsessive-compulsive disorders.

According to a fifth aspect of the invention there is provided a compound having the formula I

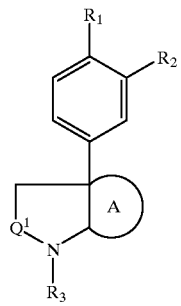

wherein the ring A is selected from the group consisting of:

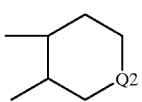 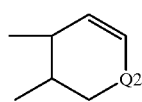 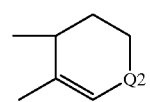

$R_1$ and $R_2$ are independently selected from H, OH, $OCH_3$ and $O(CH_2)_nCH_3$;

$R_3$ is selected from H, $CH_3$ and $(CH_2)_nCH_3$;
n is an integer from 1 to 6;
and $Q_1$ and $Q_2$ are independently selected from $CH_2$, C=O and CHOH;
with the provisos that:
(1) when the ring A is

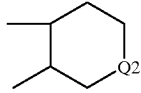

$R_1$ and $R_2$ are $OCH_3$, $R_3$ is $CH_3$, and $Q_1$ is $CH_2$, then $Q_2$ is not C=O or CHOH;
(2) when the ring A is

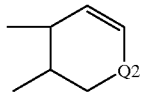

$R_1$ and $R_2$ are $OCH_3$ or $R_2$ is OH and $R_2$ is H, $R_3$ is $CH_3$, and
$Q_1$ is $CH_2$, then $Q_2$ is not C=O; and
(3) when the ring A is

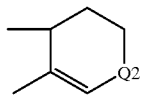

$R_1$ and $R_2$ are $OCH_3$, $R_3$ is $CH_3$, and $Q_1$ is C=O, then $Q_2$ is not C=O.

DESCRIPTION OF EMBODIMENTS

Figure 1:
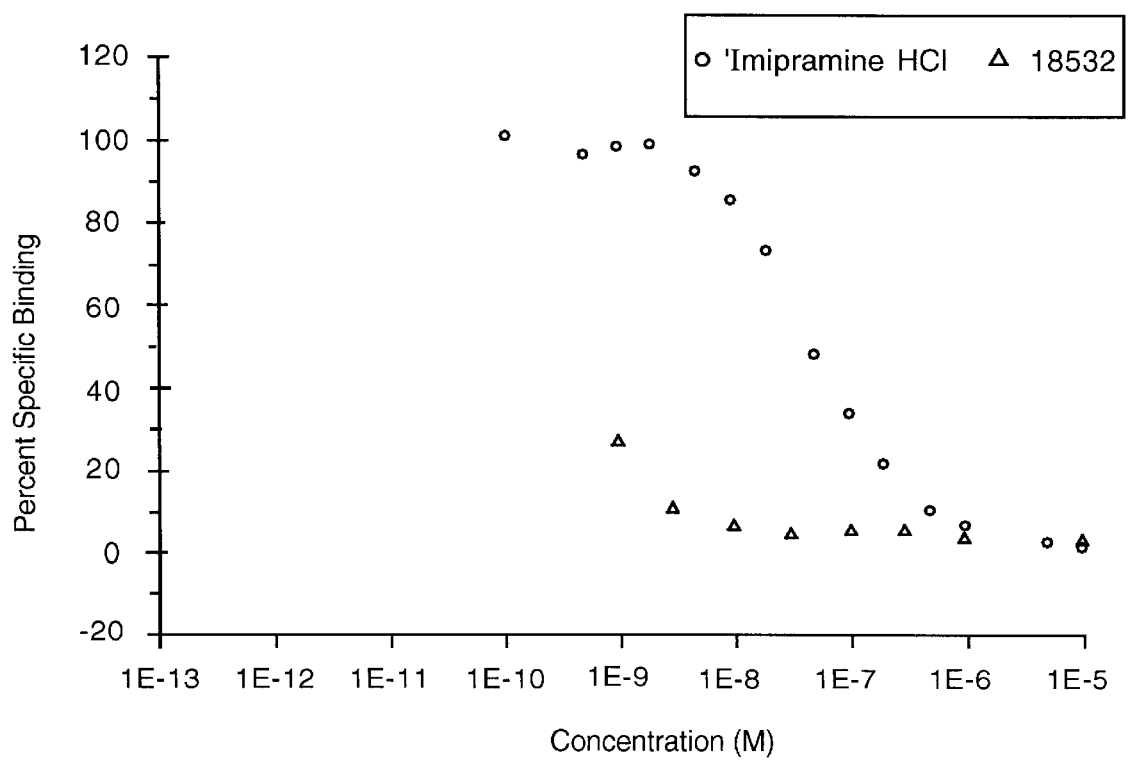
FIG. 1 is a graph for a serotonin-uptake assay comparing (−)-mesembrine, identified by the code number 18532, as compared with the known serotonin-uptake inhibitor imipramine HCl.

The first aspect of the invention is the use of compounds of the formula I as serotonin-uptake inhibitors.

The compounds of the formula I may be utilised in either of their isomeric forms i.e as the (−)isomer or as the (+)isomer, or as the racemic mixture of the two isomers. The preferred form is the (−)isomer.

The compounds of the formula I may be divided into three sub groups:

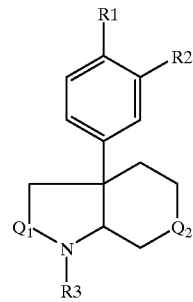

I.1

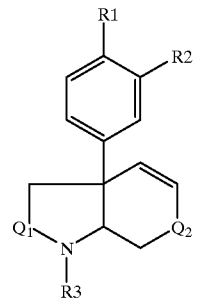

I.2

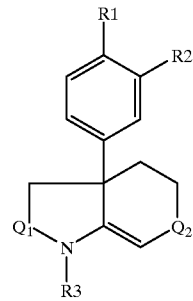

I.3

In the compounds of the formula I, preferably $R_1$ and $R_2$ are both $OCH_3$, $R_3$ is $CH_3$, $Q_1$ is $CH_2$ and $Q_2$ is selected from C=O and CHOH.

The preferred compound of formula I.1, is that in which $R_1$ and $R_2$ are $OCH_3$, $R_3$ is $CH_3$, $Q_1$ is $CH_2$ and $Q_2$ is C=O. This is the compound known as mesembrine.

The structure of mesembrine, also known as 3a-(3,4-dimethoxyphenyl)-octahydro-1-methyl-6H-indol-6-one, has been reported by Popelak et al., Naturwiss.47,156 (1960), and the configuration by P W Jeffs et al., J.Am.Chem.Soc.91,3831 (1969).

Mesembrine is preferably used as its (−)-isomer i.e (−)-mesembrine.

Another preferred compound of the formula I.1 is that in which $R_1$ and $R_2$ are $OCH_3$, $R_3$ is $CH_3$, $Q_1$ is $CH_2$ and $Q_2$ is CHOH, i.e the compound known as mesembranol.

Preferred compounds of the formula I.2 are those in which $R_1$ is selected from OH and $OCH_3$, $R_2$ is selected from H and $OCH_3$, $R_3$ is $CH_3$, $Q_1$ is $CH_2$ and $Q_2$ is C=O.

A particularly preferred compound of the formula I.2 is that in which $R_1$ and $R_2$ are $OCH_3$, $R_3$ is $CH_3$, $Q_1$ is $CH_2$ and $Q_2$ is C=O, i.e the compound known as mesembranone.

The preferred compounds of the formula I.3 are those in which $R_1$ and $R_2$ are $OCH_3$, $R_3$ is $CH_3$, and $Q_1$ and $Q_2$ are C=O.

As stated above, it has been known that mesembrine is useful as a medicament having CNS stimulating action.

However, it has now been discovered that the compounds of the invention have a totally different mode of action as serotonin-uptake inhibitors, and in specified doses act as anti-depressants, minor tranquilizers and anxiolytics.

Thus, the compounds of the formula I are useful in the treatment of diseases selected from the group consisting of mild to moderate depression, psychological and psychiatric disorders where anxiety is present, major depressive episodes, alcohol and drug dependence, bulimia nervosa, and obsessive-compulsive disorders.

The second aspect of the invention is a pharmaceutical composition in unit dosage form comprising a serotonin-uptake inhibitor having the formula I as set out above, in a unit dose of from 20 micrograms to 2 milligrams inclusive, preferably from 50 micrograms to 500 micrograms inclusive, more preferably from 100 micrograms to 300 micrograms inclusive, preferably as a once-a-day administration.

The compounds of the formula I may be formulated in any suitable form for pharmaceutical administration, such as for example aqueous-ethanolic tinctures, tablets, capsules, nasal sprays and skin-patches. The formulations may be designed to be taken orally sublingually, intra-nasally and transdermally.

The third aspect of the invention is a method of treating diseases that respond to treatment with a serotonin-uptake inhibitor comprising administering to a patient in need thereof an effective amount of a compound having the formula I, in the doses described above.

The preferred compound for the pharmaceutical composition and for the method as described above is (−)-mesembrine, with mesembranol and mesembranone also being preferred.

The fourth aspect of the invention is a pharmaceutical composition comprising as an active ingredient plant material or an extract of a plant of the family Mesembryanthemaceae, more preferably a plant of the genus Sceletium, most preferably a plant of the species Sceletium tortuosum(L.) N.E. Br., containing in each unit dose an amount of 20 micrograms to 2 milligrams inclusive, preferably from 50 micrograms to 500 micrograms inclusive, more preferably from 100 micrograms to 300 micrograms inclusive, of a compound selected from the group consisting of mesembrine, mesembranol and mesembranone, or a mixture of two or more thereof.

In other words, this pharmaceutical composition, while derived from a natural plant material, must contain a known and specified content of the active component or components.

The pharmaceutical composition of the invention may comprise fresh or dry portions of the plant, ground to a pulp or powder, or an aqueous or alcoholic extract of the plant, all containing amounts of mesembrine, mesembranol or mesembranone.

Again, the pharmaceutical composition may be formulated for example as an aqueous-ethanolic tincture, tablet, capsule, nasal spray or skin-patch for oral, sublingual, intra-nasal and transdermal application.

Methods for the extraction of (−)-mesembrine from a plant material containing the product, and methods of analysis thereof are set out below.

1 EXTRACTION METHODS

Dry material:

Material (or alcoholic extracts) are air-dried at maximum 40° C. before analysis. Yield figures for mesembrine are variable but are typically between 15 and 35 mg per gram dry leaves (mean value around 15 mg per gram dry weight). Finely ground material (pestle and mortar) is mixed with 15 ml 0.05 M $H_2SO_4$ and left standing at room temperature for 20 minutes. After filtration, the remaining solids are re-extracted with 5 ml 0.05 M $H_2SO_4$. The aqueous phases are combined, applied to glass columns with a coarse grade celite (24 g), alkalinized with ammonia (4 ml) and extracted (1X) with 100 ml $CH_2Cl_2$. The $CH_2Cl_2$ extracts are dried with anhydrous $Na_2SO_4$ and the solvent evaporated under reduced pressure to leave the alkaloid as a pale brown oil. The alkaloids can also be extracted with hot or cold water instead of $H_2SO_4$, or with methanol, ethanol, acetonitrile, chloroform or dichloromethane.

Fresh material:

The leaf sap of fresh leaves (or alcoholic extracts) can be studied directly, or the alkaloids may be directly extracted in hot or cold water, ethanol, ethanol/acetonitrile, chloroform or dichloromethane or any other suitable solvent. For HPLC or GC, the sample has to be filtered (eg 0.45 $\mu$m filter) in order to protect the columns from impurities. Yield figures for mesembrine are variable, but are typically between 0.8 and 6.5 mg per ml leaf sap (mean value around 3.3 mg per ml).

2 METHODS OF ANALYSIS 2.1 Thin-layer Chromatography

This method can be used only for rough screening purposes, as there is a poor separation between mesembrine alkaloids with a 4.5 double bond (such as mesembrenone) and those without (such as mesembrine). For routine screening, the following system is suitable (Rf of mesembrine=0.6): Merck 60 F254 silica gel plates (0.25 mm layer thickness) developed in $CHCl_3$:cyclohexane:$Et_2NH$ (4:5:1). The plates are dried at 100° C. for 3 minutes, studied under UV254 and UV365 and then sprayed with iodoplatinate or dragendorff spray reagents.

2.2 Gas Chromatography (GC)

Extracts are dissolved in minimum MeOH and studied by comparative GC and GC-MS. Authentic mesembrine should be used as external standard to quantify the alkaloid content.

A Routine analyses for large numbers of samples (fast system): DB-1 fused silica capillary column (30 m×0.25 mm internal diameter; He as carrier gas at 4 ml min$^{-1}$; column temperature 200° C. to 300° C. at 100 min$^{-1}$, 15 minute isotherm; injector 230° C.; FID (Flame Ionization Detector) detection 300° C.; split ratio 30:1; injection volume 1 $\mu$l ).

B High resolution analyses (selected samples, slow): DB-1 fused silica capillary column (30 m×0.25 mm internal diameter; He as carrier gas at 4 ml min$^{-1}$; column temperature 150° to 320° C. at 60 min$^{-1}$ 15 minute isotherm; injector 230° C.; PND (Phosphorus-Nitrogen Detector) detection 300° C.; split ratio 30:1; injection volume 1 $\mu$l).

C For GC-MS: Typical system such as DB-1 fused silica capillary column (30 m×0.32 mm internal diameter; He as carrier gas; column temperature 150° to 300° C. at 60 min$^{-1}$, split ratio 20:1; injection volume 1 $\mu$l).

2.3 High Performance Liquid Chromatography (HPLC)

A phenomenex IB-Sil column is used (C18 reverse phase, 5 $\mu$m particle size, 250 mm×4.6 mm internal diameter, flow rate 1 ml per minute, 20 $\mu$l sample loop).

An isocratic solvent system comprising 30% A in B (A=1% triethylamine in water; B=60% acetonitrile). Total run time is 10 minutes. Detection by diode array detector, using two channels (A set at 280±30 nm, B set at 292±10 nm). Results expressed in mg mesembrine per ml leaf sap (calculated from detector response, mean value of channels A and B). For concentrations below 0.05 mg per ml, channel A is more accurate (lower detection limit of ca. 0.01 mg per ml leaf sap). The method depends on a calibration curve which was calculated using five different concentration levels of pure mesembrine, using the System Gold (Beckman) software package. For yield figures see 'fresh material extraction'.

3 IDENTIFICATION OF MESEMBRINE BY MASS SPECTROMETRY AND 1H NMR SPECTROSCOPY

In the two populations of Sceletium tortuosum studied, mesembrine occurs in leaves as virtually the only compound (small but negligible amounts of mesembrenone and mesembrenol may sometimes be present). The alkaloid was isolated from the leaves using the methods described above and fully identified by mass spectrometry (relative structure) and 1H NMR spectroscopy (absolute configuration). The optical rotation was measured, which confirmed that the natural product is the (−)-form.

Mesembranol and mesembranone may be extracted from suitable plant material, analysed and identified as set out above for mesembrine.

Derivatives of mesembrine, mesembranol and mesembranone, within the group of compounds of formula I, may be prepared from these starting compounds by methods known in the art.

Higher order alkyl ethers of mesembrine, mesembranone or mesembranol may be prepared by acidolytic cleavage of the methoxy methyl groups (for example using anhydrous hydrogen fluoride) which gives the corresponding hydroxyl compound ($R_{1,2}$=OH) followed by alkylation using the appropriate alkyl halide (for example $CH_3(CH_2)_n Br$).

The hydroxyl compounds above may be reduced to the corresponding benzyl compound ($R_{1,2}$=H) by catalytic hydrogenation (for example over palladium).

Mesembranol may be prepared from mesembrine by catalytic hydrogenation (for example over palladium).

Compounds of formula I.3 may be prepared from the appropriate mesembrine derivatives described above by dehydrogenation with mecuric acetate.

Compounds of formulas I.2 and I.3 may be prepared from mesembrine by oxidation using selenium dioxide ($SeO_2$) in tertiary butanol with subsequent purification of the desired positional isomer.

The isolated pure compound (−)-mesembrine was screened for biological activity by the National Institute of Mental Health in the United States of America, through a contract with Novascreen, a division of Oceanix Biosciences Corporation. As illustrated in FIG. 1, in comparison to the tricyclic anti-depressant imipramine HCl, (−)-mesembrine was found to be a highly potent serotonin-uptake inhibitor with an IC50 in nano-molar concentrations.

This testing of (−)-mesembrine also gave the following results set out in Table 1, and below.

TABLE 1

| Receptor | Percent Inhibition (Average: N = 2) Concentration 5,0E1 |
| --- | --- |
| GABA B | −0,6% |
| Serotonin-uptake | 96,5% |

The inhibitory constant (Ki) of (−)-mesembrine, with reference to imipramine HCl was found to be Ki=3.6E-8.

Figure 2:
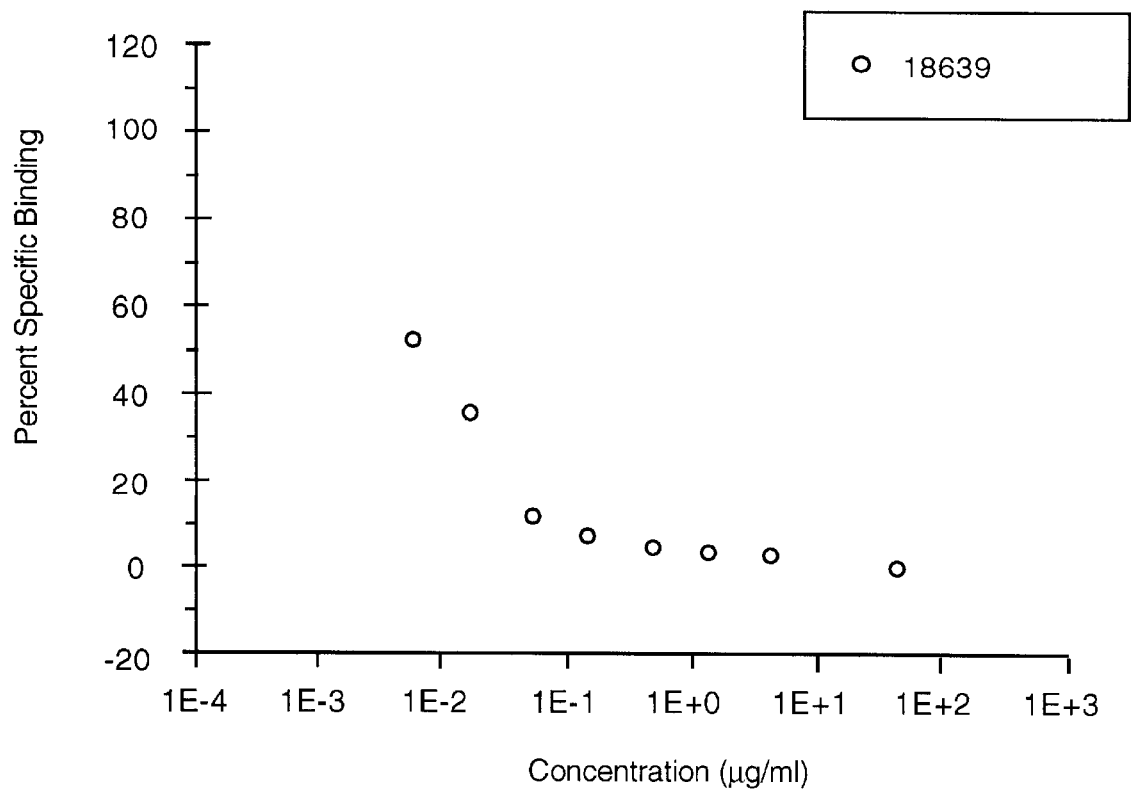
FIG. 2 is a graph for a serotonin-uptake assay of a whole plant extract of a plant from the family Mesembryanthemaceae, identified by the code number 18639, as well as some comparisons with the known serotonin-uptake inhibitor imipramine HCl.
Figure 3:
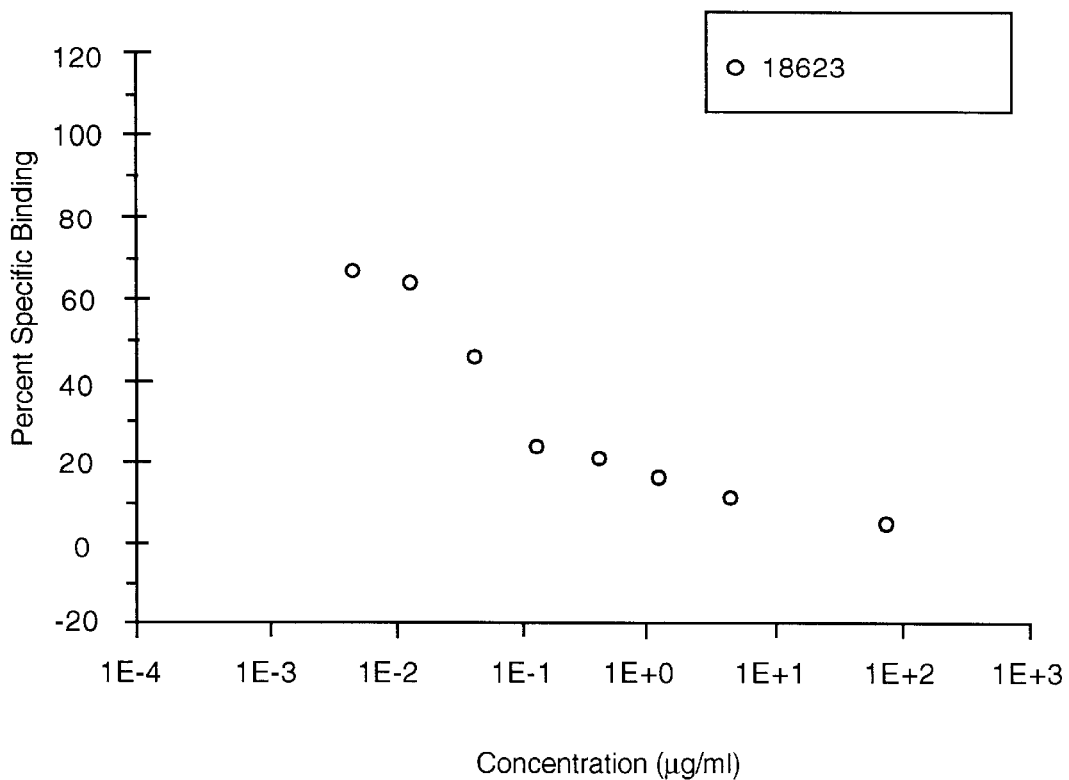
FIG. 3 is a graph for a serotonin-uptake assay for mesembranol, identified by the code number 18623, as well as some comparisons with the known serotonin-uptake inhibitor imipramine HCl.
Figure 4:
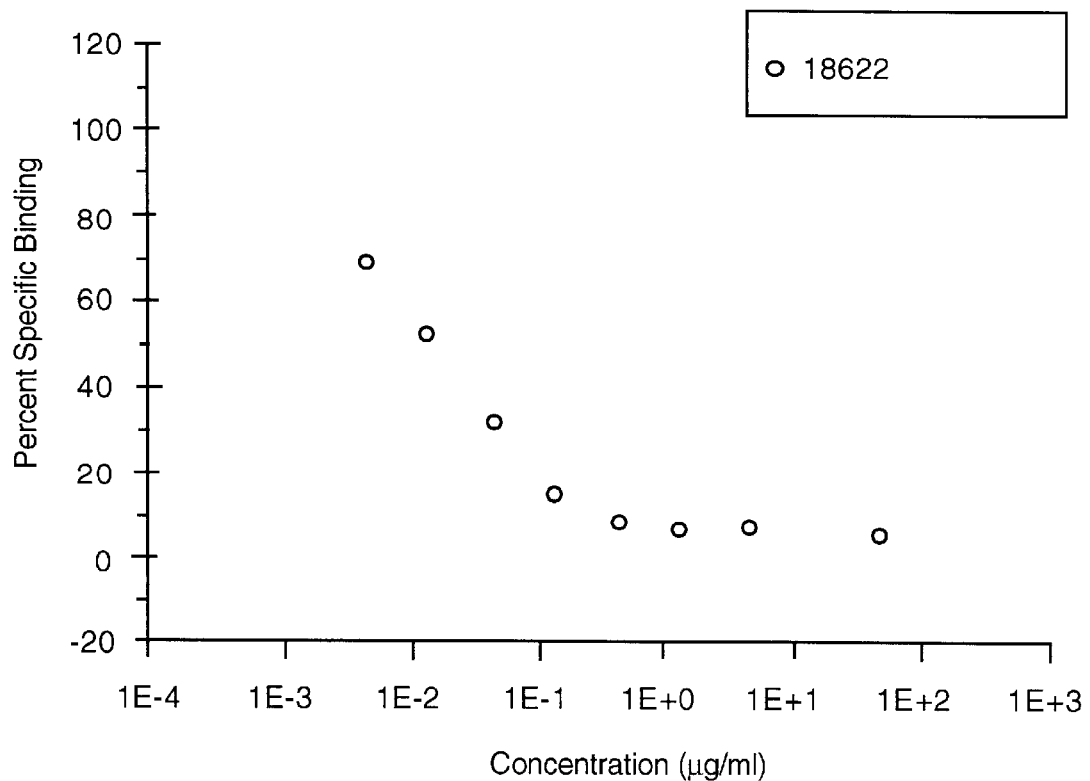
FIG. 4 is a graph for a serotonin-uptake assay for mesembranone, identified by the code number 18622, as well as some comparisons with the known serotonin-uptake inhibitor imipramine HCl.

In addition, the whole plant extract of Sceletium N.E.Br., mesembranol and mesembranone were screened for biological activity by the National Institute of Mental Health in the United States of America through the contract with Novascreen. The results of these assays are illustrated in FIGS. 2 to 4. These assays show that the whole plant extract, as well as mesembranol and mesembranone are highly potent serotonin-uptake inhibitors.

Various in vitro studies of the effects of the compounds of the invention were carried out in adult volunteers as follows:
Study 1. N=3 Healthy Adult Volunteers, All Health Professionals Sep. 13, 1996.

A single dose of standardised preparation of dried whole plant, standardised to contain 400 micrograms of mesembrine was taken sublingually.

Rapid onset of action (10–15 minutes) noted by all.
Anxiolytic effect noted by all.
Sustained elevation of mood noted by all.
Duration of anxiolytic action ranged from five hours to eight hours.
Study 2. N=2 Healthy Adult Volunteers, All Health Professionals Sep. 21, 1996.

A single 200 microgram dose of pure (−)-mesembrine dissolved in 1 ml of 60% ethanol was taken sublingually.

Rapid onset of action (7 and 12 minutes, respectively) noted by both.
Anxiolytic effect noted by both.
Sustained elevation of mood noted by both (for approximately eight hours and eleven hours respectively)
Duration of anxiolytic action ranged from five hours to eight hours.
Study 3. N=2 Adult Volunteers, Both Self-confessed Alcoholics and Polysubstance Abusers Sep. 21, 1996.

A single 5 ml dose of a whole-plant aqueous-ethanolic extract containing 100 micrograms of mesembrine per ml of extract (60% ethanol) was administered orally (total dose of mesembrine 500 micrograms).

Rapid onset of action (15–20 minutes) noted by both.
Anxiolytic effect noted by both.
Neither volunteer imbibed alcohol or used any illicit or other drug for a twenty-four hour period following the administration of the single dose.

Examples of pharmaceutical compositions of the invention will now be given.

EXAMPLE 1

A liquid composition comprises a 60% ethanol/water solvent containing about 200 μg/ml of (−)-mesembrine.

A typical dose of the liquid composition is from 1 ml to 5 ml inclusive daily.

EXAMPLE 2

A sublingual tablet contains a spray-dried 30% aqueous-ethanolic extract of Sceletium tortuosum, containing 200 micrograms of (−)-mesembrine, and conventional pharmaceutical excipients.

EXAMPLE 3

An oral tablet contains 200 micrograms of pure (-)-mesembrine, and conventional pharmaceutical excipients.

What is claimed is:

1. A pharmaceutical composition in unit dosage form comprising a serotonin-uptake inhibitor having the formula I

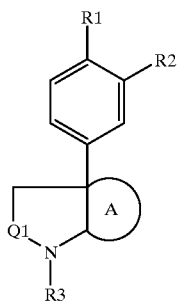

wherein the ring A is selected from the group consisting of:

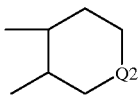 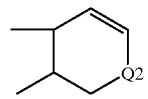 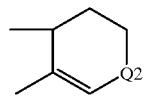

$R_1$ and $R_2$ are independently selected from H, OH, $OCH_3$ and $O(CH_2)_nCH_3$;

$R_3$ is selected from H, $CH_3$ and $(CH_2)_nCH_3$;

n is an integer from 1 to 6; and $Q_1$ and $Q_2$ are independently selected from $CH_2$, C=O and CHOH; in a dose of from 20 micrograms to 2 milligrams.

2. A pharmaceutical composition according to claim 1 comprising the serotonin-uptake inhibitor in a dose of from 50 micrograms to 500 micrograms.

3. A pharmaceutical composition according to claim 1 or 2 wherein the serotonin-uptake inhibitor is (-)-mesembrine.

4. A method of treating diseases that respond to treatment with a serotonin-uptake inhibitor comprising administering to a patient in need thereof an effective amount of a serotonin-uptake inhibitor having the formula I

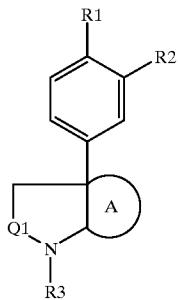

wherein the ring A is selected from the group consisting of:

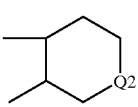 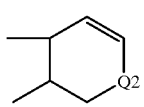 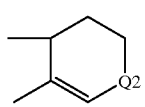

$R_1$ and $R_2$ are independently selected from H, OH, $OCH_3$ and $O(CH_2)_nCH_3$;

$R_3$ is selected from H, $CH_3$, and $(CH_2)_nCH_3$;

n is an integer from 1 to 6; and $Q_1$ and $Q_2$ are independently selected from $CH_2$, C=O and CHOH.

5. A method according to claim 4 wherein the serotonin-uptake inhibitor is administered in a unit dose of from 20 micrograms to 2 milligrams.

6. A method according to claim 5 wherein the serotonin-uptake inhibitor is administered in a unit dose of from 50 micrograms to 500 micrograms.

7. A method according to any one of claims 4 to 6 wherein the serotonin-uptake inhibitor is (-)-mesembrine.

8. A pharmaceutical composition comprising as an active ingredient plant material or an extract of a plant of the family Mesembryanthemaceae containing in each unit dose an amount of from 20 micrograms to 2 milligrams of a compound selected from the group consisting of mesembrine, mesembranol and mesembranone, or a mixture of two or more thereof.

9. A pharmaceutical composition according to claim 8 wherein each unit dose contains an amount of from 50 micrograms to 500 micrograms of the compound.

10. A method of treating a patient suffering from a disease, said method comprising administering to said patient a composition comprising a plant material or an extract of a plant of the family Mesembryanthemaceae containing in each unit dose an amount of from 20 micrograms to 2 milligrams of a compound selected from the group consisting of mesembrine, mesembranol and mesembranone, or a mixture of two or more thereof wherein said disease is selected from the group consisting of mild to moderate depression, psychological and psychiatric disorders where anxiety is present, major depressive episodes, alcohol and drug dependence, bulimia nervosa, and obsessive-compulsive disorders.

11. The method of claim 10 wherein each unit dose contains an amount of from 50 micrograms to 500 micrograms of the compound.

* * * * *

UNITED STATES PATENT AND TRADEMARK OFFICE
CERTIFICATE OF CORRECTION

PATENT NO.    : 6,288,104 B1                                            Page 1 of 1
DATED         : September 11, 2001
INVENTOR(S)   : Nigel Peter Gericke and Ben-Erik Van Wyk It is certified that error appears in the above-identified patent and that said Letters Patent is hereby corrected as shown below:

<u>Title page,</u>
Item [56], OTHER PUBLICATIONS,
In Jeffs et al., insert after "of" and before "(±)" -- (±) Mesembrine --.
In Kruger et al., delete "N-Demthylmesembranol," and replace with -- N-Demethylmesembranol,".
In Smith et al., delete "otehr" and replace with -- other --.

Item [57], ABSTRACT,
Line 2, delete "scrotonin" and replace with -- serotonin --.

<u>Column 1,</u>
Line 27, delete "over 300 year" and replace with -- over 300 a year --.

<u>Column 2,</u>
Line 6, delete "ie" and replace with -- i.e. --.
Line 24, after "plant" delete "of" and replace with -- of the --.
Line 38, delete "ie" and replace with -- i.e. --.

<u>Column 3,</u>
Line 23, delete "or $R_2$ is OH" and replace with -- or $R_1$ is OH --.

Signed and Sealed this

Twenty-fifth Day of June, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,288,104 B1
DATED : September 11, 2001
INVENTOR(S) : Nigel Peter Gericke and Ben-Erik Van Wyk It is certified that error appears in the above-identified patent and that said Letters Patent is hereby corrected as shown below:

<u>Title page,</u>
Item [73], Assignee, change "African Natural Health CC" to
-- Pharma Natura (Proprietary) Limited --

Signed and Sealed this

Tenth Day of September, 2002

Attest:

Attesting Officer

JAMES E. ROGAN
*Director of the United States Patent and Trademark Office*